United States Patent [19]

Stinger

[11] Patent Number: 5,634,913
[45] Date of Patent: Jun. 3, 1997

[54] SOFTENING CONDUIT FOR CARRYING FLUIDS INTO AND OUT OF THE HUMAN BODY

[76] Inventor: Florence Stinger, 1117 Highwood Rd., Rockville, Md. 20851

[21] Appl. No.: 590,317

[22] Filed: Jan. 23, 1996

[51] Int. Cl.$^6$ .................................................. A61M 5/32
[52] U.S. Cl. ........................... 604/272; 604/110; 604/167; 604/256
[58] Field of Search .................. 604/30–1, 33–4, 604/51–2, 93, 110, 158, 164, 167, 169, 188, 190, 200–1, 205–6, 213, 218, 226, 240, 244–7, 256, 264–5, 272, 274, 281, 283; 128/760, 763–6, 770

[56] References Cited

U.S. PATENT DOCUMENTS

| | | | |
|---|---|---|---|
| 4,816,021 | 3/1989 | Johnson | 604/110 |
| 4,838,877 | 6/1989 | Massau | 604/272 |
| 4,955,863 | 9/1990 | Walker et al. | 604/165 |
| 5,102,401 | 4/1992 | Lambert et al. | 604/264 |
| 5,108,380 | 4/1992 | Herlitze et al. | 604/169 |
| 5,229,211 | 7/1993 | Murayama et al. | |
| 5,250,066 | 10/1993 | Lambert | |
| 5,322,518 | 6/1994 | Schneider et al. | 604/247 |
| 5,441,489 | 8/1995 | Utsumi et al. | 604/280 |
| 5,520,666 | 5/1996 | Choudhury et al. | 604/283 |

OTHER PUBLICATIONS

Shape Memory Polymer, Memry Corporation, 9 pages, May 25, 1993.

Thromboresistant, Radiopaque, Softenable Thermoplastic Catheter, Ward et al, 2nd World Congress on Biomaterials, Apr. 27–May 1, 1984, p. 55.

Shape Memory PUR Enhances New Product Development, Modern Plastics, No. 72, No. 5, May 1995.

Mitsubishi Shape Memory Polymer™, Mitsubishi Heavy Industries, Ltd.

Shape Memory Polymer®, Memry Corporation.

SMP Passes Key Tests, Mitsubishi Heavy Industries, Ltd., 011894.42.

Room–Temperature–Functional Shape–Memory Polymers, Plastics Engineering, Feb. 1995, pp. 29–31.

*Primary Examiner*—Michael Powell Buiz
*Assistant Examiner*—Bhisma Mehta
*Attorney, Agent, or Firm*—Patrick O'Reilley

[57] ABSTRACT

A medical device for introducing fluid treating material to or removing a fluid material from a body cavity of a human or animal, including:

- a hollow, needle-like structure having a proximal end and a distal end, the proximal end having a beveled tip and being formed from a polymer which is sufficiently rigid at ambient temperature to permit puncture of skin by the beveled tip, and which becomes soft after a predetermined period of time exposed to body temperature and body fluids, thus preventing bodily trauma; and
- a hub attached to the distal end of the hollow needle-like structure and having a diameter greater than that of the hollow needle-like structure, the hub including a connector for attachment of a handle or a device for introducing fluid treating material to or removing fluid from the body cavity.

27 Claims, 3 Drawing Sheets

SOFTENING CONDUIT FOR CARRYING FLUIDS INTO AND OUT OF THE HUMAN BODY

BACKGROUND OF THE INVENTION

1. Field of the Invention

The invention relates to the field of catheters and similar devices used for introducing materials into or removing materials from the bodies of humans and animals.

2. Description of Related Art

Hypodermic needles and lancets have not changed substantially over the past 100 years. For the most part, they are constructed as a hollow, metal, needle-like structure with a bevelled tip, and as such they are quite dangerous. Such needles are involved in the transmission of diseases through "needle sticks" of health care workers, and can break during use, requiring surgical removal.

Needle stick injuries account for approximately 80% of all accidental exposures to blood by health care workers. About 20% of the injuries occur before or during the use of needles, up to 70% occur after use and before disposal (mostly in association with recapping) and the remainder occur during or after disposal.

During the past few years, many new devices intended to reduce the chance of percutaneous injuries have been evaluated. However, the results have been disappointing, and it is not clear that any of the devices have reduced injury rates or have been acceptable to users. Some of the devices have introduced new problems.

Moreover, metal needles, lancets and guidewires are difficult to destroy since they cannot be burned by ordinary means and pose a continuing disposal and health problem. They must be disposed of in separate "sharps" containers and due to the disposal problems have occasionally been disposed of by illegal dumping.

In the past, needle guards have been proposed to reduce the danger of metal hypodermic needles. However, these needle guards have proven to be unwieldy, too costly and inconvenient to use, and injuries have resulted from positioning such needles guards after use of the needles.

Several proposals have been made recently to reduce the hazards associated with metal needles. U.S. Pat. No. 4,976,704 discloses a hypodermic needle made primarily from a metal alloy that loses its rigidity upon exposure to moisture, so that it becomes incapable of repenetrating the skin. The only material disclosed for this use is a particular proprietary machinable aluminum alloy.

U.S. Pat. No. 4,838,877 discloses an injection device constructed of a polymeric material, and U.S. Pat. No. 5,458,614 discloses a needle or a lancet made from a flexible polymeric material which will not pierce the skin by itself, but which is stiffened and made to more readily pierce the skin by working in conjunction with an augmenting structure.

In the field of catheters, it has been proposed to utilize a polymer material which softens at body temperature and/or upon exposure to moisture. Such catheters are disclosed, for example, in U.S. Pat. Nos. 4,846,812 and 5,441,489, and comprise a rigid portion for manipulation of the catheter and a portion which becomes flexible after insertion into the body. This flexibility can be delayed for a period of time to enable the catheter to be properly positioned.

However, when puncturing of the skin is necessary, it is still necessary to make an incision or to puncture the skin with a separate lancet. For example, U.S. Pat. Nos. 4,883,699 and 4,911,691 disclose a catheter formed of a polymer which softens upon absorbing water used in combination with a metal lancet which passes therethrough for puncturing the skin. U.S. Pat. No. 4,955,863 similarly discloses a catheter assembly including a cannula, a needle and a catheter inserter in slidable relationship to the cannula. These devices present the disadvantage that metal lancets are necessary, presenting the safety and disposal problems discussed above. Further, the lancet or guidewire used in connection with the catheter is necessarily longer than the catheter itself, and enters the body first, at which time the practitioner must push the lancet or guidewire further in order to correctly position the catheter. This procedure is a risk to the patient, as the lancet or guidewire may puncture a vessel, membrane, tendon, bone, nerve, lung or spinal cord. Early detection of the appropriate placement of the catheter is not possible with these devices combining a metal lancet or guidewire with a catheter.

SUMMARY OF THE INVENTION

Thus, it is an object of the invention to provide a catheter which eliminates the use of metal lancets, guidewires and needles.

It is a another object of the invention to provide a catheter which does not use a separate lancet, needle or guidewire for puncturing the skin.

It is a further object of the invention to provide a means for puncturing the skin which does not require disposal in a sharps container, reducing the cost of disposal, and which can be destroyed by burning.

These and other objects of the invention can be achieved with the use of a catheter formed at least in part from a polymeric material which is normally rigid and has a bevelled tip, preferably v-shaped and bilateral, for puncturing the skin, but which softens when exposed to heat and/or moisture in the bodies of humans and animals. The angle of the bevel is typically 10°–15° and the softening of the catheter can be delayed for a period of time to enable proper placement.

The invention thus comprises a hollow, needle-like structure having a proximal end and a distal end, the proximal end having a bevelled tip and being formed from a polymer which is sufficiently rigid at ambient temperature to permit puncture of skin by the bevelled tip, and which becomes soft after a predetermined period of time exposed to body temperature and body fluids in order to prevent bodily trauma; and a hub attached to the distal end of the hollow needle-like structure and having a diameter greater than that of the hollow needle-like structure, the hub including connector means for attachment of a handle or a device for introducing fluid treating material to or removing fluid from the body cavity.

According to the invention, the polymeric needle-like structure is substantially rigid at ambient (room) temperature, and does not become flexible and soft until it is inserted in the body. Because the structure remains rigid, it is able to puncture the skin unaided by rigidifying means as were used in the prior art. Moreover, because there is not a separate lancet or needle for puncturing the skin which must be subsequently removed and replaced by the catheter, it is possible to construct catheters of greatly improved design which will limit the possibility of needle sticks and reduce the possibility of health care workers coming into contact with blood. In particular, it is possible to construct a catheter including a normally-closed valve, which opens only when tubing, an injection cap or a syringe is attached to the catheter.

It is also possible to engineer the polymer for particular properties other than simply softening temperature. For example, it is possible to alter the glass transition period of the polymer in order to determine the length of time the catheter will remain rigid after insertion. Thus, the catheter can be made to stay rigid for 2–9 minutes after insertion, to be useful in a peripheral catheter insertion procedure. The catheter can also be made to stay rigid for 10–90 minutes after insertion to allow the health care practitioner to insert a lumbar line, central line, chest tube, or other device where an extended period of rigidity is useful. Further it is possible to utilize polymers which permanently lose their rigidity after exposure to heat and moisture, and which therefore do not present a hazard after removal from the patient, and which can not be reused. This is particularly useful in preventing IV drug abuse.

Because a separate needle or lancet is not used, the catheter of the invention may be made in a smaller diameter with conical points, resulting in less trauma and pain during the insertion. Once in the body, the catheter will absorb fluid and swell to a larger diameter for fluid flow. The swelling and softening reduces irritation of the intima (lining of the vein) and mechanical phlebitis, or infiltration of the vein, is therefore less likely. The swelling of the catheter can result in pressure at the wound site, reducing bleeding and bacterial invasion into the wound. The swelling also prevents the catheter from slipping out.

Numerous polymers are known which are hard enough to puncture skin, but which will soften under exposure to heat and moisture. Among these polymers are polysaccharides, alginates, and starch polymers. The particularly preferred polymers are shape memory polyurethanes, as disclosed in the aforementioned U.S. Pat. No. 5,441,489, which is hereby incorporated by reference, as well as in Japanese Published Patent Applications Nos. 61-293214, 63-244341 and 63-260491. The polymers are available commercially from Mitsubishi Heavy Industries, Ltd. and are sold in the United States by Memry Corporation. The polymers disclosed have an average molecular weight of 200,000 to 700,000, 3 to 60% by weight of stoichiometrically calculated content of hard segments consisting of diisocyanate and glycols which are polyurethane materials, or those having a fluidization temperature of 160°–210° C. The desired polyurethanes have a glass transition temperature of about 40° C., and thus become soft within a predetermined period of time after insertion into a human or animal body, depending on the glass transition temperature.

Shape memory polyurethanes are also disclosed in U.S. Pat. Nos. 5,145,935 and 5,135,786, which are also incorporated herein by reference.

Additional information relating to these shape memory polyurethanes can be found in Shirai et al, *Development of Polymeric Shape Memory Material*, Mitsubishi Technical Bulletin No. 184, December 1988, as well as in Gordon, The Properties and Applications of Shape Memory Polyurethanes, Mat Tech, 8:254–258(1993), Frenger, *Biomedical Uses of Shape Memory Polymers*, Biomedical Sciences Instrumentation, 29:47–50 (1993)and Kusy et al, *Thermal Characterization of Shape Memory Polymer for Biomedical Implantations*, Thermochimica Acta, 243:253–263(1994).

Other polymers suitable for use according to the invention include hydrogels. Further, suitable temperature or fluid sensitive polyethylene oxide polymers are disclosed in U.S. Pat. No. 5,439,966, incorporated herein by reference. These polymers are mechanically strained, hydrophilic, semicrystalline polymers. Upon activation by exposure to a particular temperature and/or polar fluids, the polymers return to an unstrained state.

The polymers according to the invention may contain additives and coatings as are known in the art. For example, the polymer will typically contain a radiopaque filler such as barium sulfate which enables the tip to be seen under fluoroscopy. The tip can be coated with silicone to allow easier placement and decreased skin drag, which decreases the pain of insertion. Moreover, the tip can also contain a hydrophobic coating to prevent kinking or accordioning of the catheter during insertion and a broad spectrum antibiotic to kill any bacteria which may enter from normal flora on the skin surface during insertion. There can also be a broad spectrum antibiotic on the interior portions of the hub and the valve elements to prevent the growth of bacteria which comes into contact with blood. The interior portions and valve elements can also contain an antithrombogenic agent to prevent clotting of the blood.

All of the polymers according to the invention have the advantage that they can be destroyed or rendered harmless by incineration at reasonable temperatures, and do not require landfill disposal.

Moreover, it is expected that the catheters of the invention will be cheaper to produce than standard catheters which require a metal needle, guidewire or lancet.

The invention is useful in the production of both straight (coring) needles and non-coring needles, which are bent in order to reduce the coring of self-sealing materials, particularly in conjunction with implanted ports such as the Port-a-Catch Catheter. When a non-coring needle is pulled out of an implanted port, the health care provider is at great risk of a needle stick in the hand holding down the implanted port. The device according to the invention softens and swells to prevent leakage of blood and fluid from the implanted port, and to keep the needle in place, and prevents needle sticks when the softened needle is removed from the implanted port.

DESCRIPTION OF THE PREFERRED EMBODIMENTS

Figure 1:
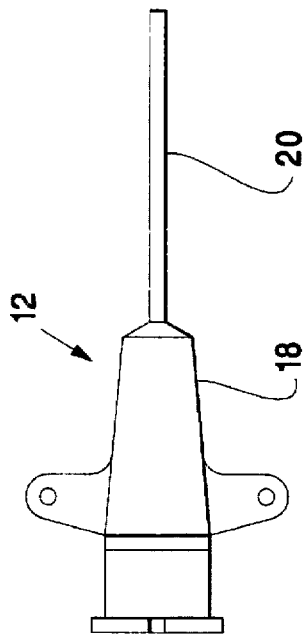
FIG. 1 is a plan view of a prior art catheter.
Figure 1:
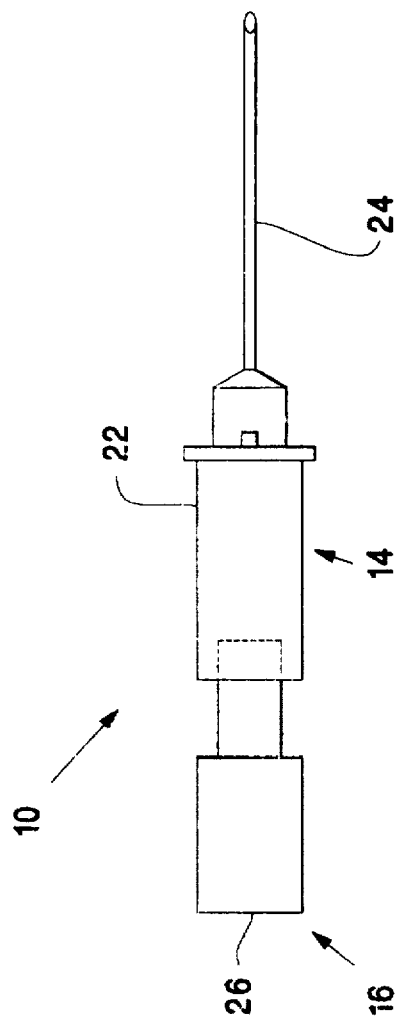

FIG. 1 shows a typical prior art catheter device used for intravenous treatments. This device 10 includes a plastic base portion 12, a piercing portion 14 and a cap portion 16.

Plastic base portion 12 includes a hub 18 and tip 20, while piercing portion 14 includes a hub 22 made of clear plastic and a hollow metal needle 24. Needle 24 is longer than tip 20, so that when the piercing portion is mated with the catheter portion, needle 24 passes through and extends beyond tip 20. Cap 16 closes off the piercing portion and includes a flash plug 26.

The prior art catheter is used as follows. With the piercing portion mated with the plastic base portion and the cap closing off the piercing portion, the metal needle is used to puncture the skin of a patient and the plastic base portion and needle are inserted into a vein. When the catheter is correctly placed, blood flows through the needle into the clear plastic hub 22 due to the flash plug allowing evacuation of air, and the blood can be observed by the user.

However, the catheter cannot be used with the needle in place, due to the risk of puncturing a vessel or causing trauma. When the needle is removed for connection of tubing or a syringe to the hub, the user can be exposed to the blood of the patient and the sharp needle, a situation which poses a threat to the health of the user.

Figure 2:
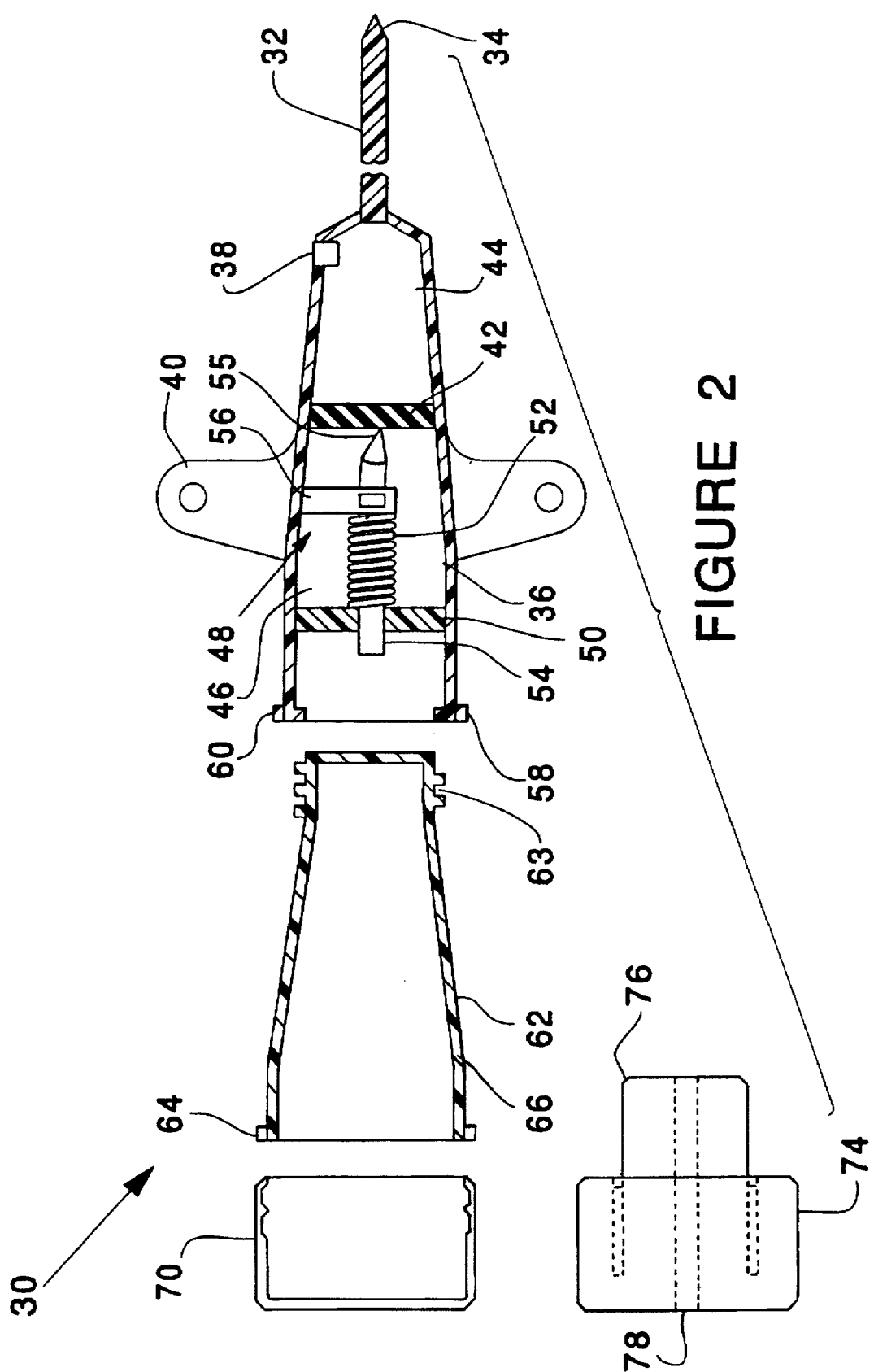
FIG. 2 is a plan view of a preferred intravenous catheter according to the invention.

FIG. 2 shows a catheter 30 of a preferred construction according to the invention. Tip 32 of catheter 30 is a hollow needle-like structure, i.e. a thin, elongated and pointed tubular structure, formed of a shape memory polymer which softens in 2–9 minutes at human body temperature, and includes a v-shaped, double bilateral beveled point 34 (coring or non-coring) for piercing the skin. The tip is attached to a hub portion 36 formed of a transparent or translucent, hard polymer, which can be any polymer approved for medical devices, and having the desired characteristics. The hub includes a flash plug 38 which permits blood to enter the hub by permitting air to leave. Wings 40 are provided to enable easier manipulation of the catheter, and to achieve stability by anchoring the wings on the skin after insertion. The catheter gauge can be marked on the wings.

A plug 42 of self-sealing material such as rubber, latex or other material such as may typically be used in connection with the dispensing of injectable medications divides the hub into a front portion 44 and a rear portion 46. Rear portion 46 includes a valve mechanism 48 including a plastic cylinder support 50, a spring 52, a hollow plastic piercing member 54 having a bent, non-coring tip 55 and a support 56. The rear end 58 of the hub includes a Luer connector 60 for receiving a syringe, injection cap or tubing, not shown.

Hollow piercing member 54 is positioned about 0.5 cm from the rear end 58 of the hub. However, when a syringe, injection cap or tubing is secured in the hub and Luer connector, flush with piercing member 54, the plastic cylinder is pushed toward the front portion 44 and the non-coring tip 55 of the piercing member is urged forward, piercing the stationary plug 42.

The rear end of the hub is fitted with a plastic handle 62 having an adaptor 64 at its rear end 66. Handle 62 is attached to the hub with an adaptor 63. The adaptor 64 is of the same size as LUER connector 60, both being externally threaded, and adaptor 64 is normally covered with a sterile plastic cap 70.

Handle 62 is provided to give the user additional maneuverability during insertion. The handle is of about the same diameter as the hub and is about 1.75 inches long.

Catheter 30 is used in the following manner. With or without handle 62 attached, spring 52 urges tip 55 of the piecing member 54 into a position at or behind the rear surface of the plug 42, leaving the plug intact. The user pierces the skin of a patient with point 34 of coring or non-coring beveled tip 32, and observes front portion 44 of transparent plastic hub 36 for a flow of blood to indicate correct placement. Due to the valve which is closed, the blood flows only to the front portion of the hub.

Once correct placement of the catheter has been confirmed, the handle 62 is removed and tubing, a syringe or an injection cap 74 is attached to the Luer connector 60 at the rear end of the hub. Attachment of the tubing, syringe or injection cap urges the non-coring tip 55 of the piercing member 54 through plug 42, allowing fluid to flow through the hollow piercing member 54, and thus between the front and rear portions of the hub 36. When the tubing or syringe is removed, the spring urges piercing member 54 rearward, and the self-sealing plug once again closes off the flow of fluid. When the valve is closed, the non-coring tip 55 returns to its position at the rear end of plug 42, and fluid flow through the plug is prevented.

Handle 62 can be taped to an IV pump or pole with the cap 70 attached, so that the user will have a sterile cap available when the tubing or syringe is removed. Since the threaded adaptor 64 is the same size as the connector 60, the cap 70 can be used to seal off the rear end of the catheter. While injection cap 74 contains a male connector 76 which opens the valve and permits an injection device to be attached at port 78, the cap 70 allows the valve to remain closed. The handle permits sterile and convenient storage of cap 70.

After 2–9 minutes of implantation, the tip of the catheter becomes softer and swells, and is more comfortable for the patient.

Other types of valves capable of stopping fluid flow when the tubing or syringe is removed can be used in connection with the catheters of the invention. One such valve is shown in U.S. Pat No. 4,190,048, and is used therein for permitting or interrupting the flow of infusate to an implanted reservoir.

Figure 3:
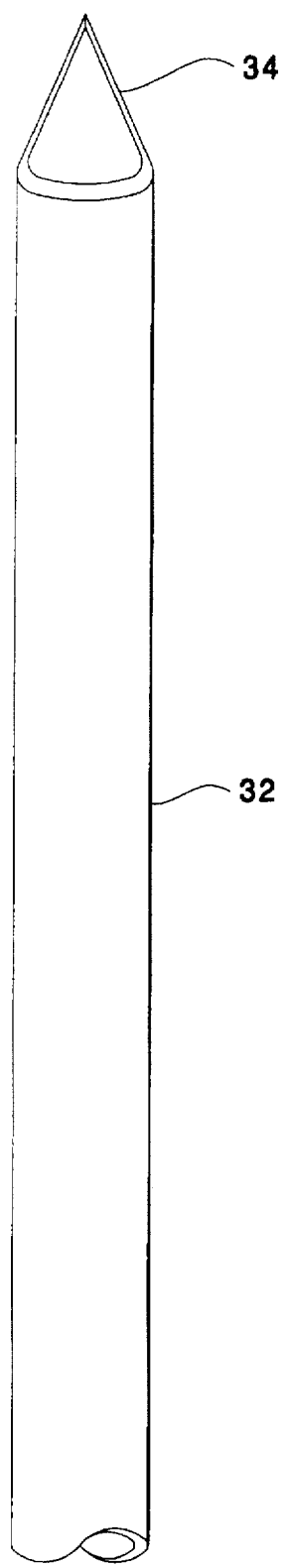
FIG. 3 is a plan view of a portion of the intravenous catheter shown in FIG. 2.
Figure 4:
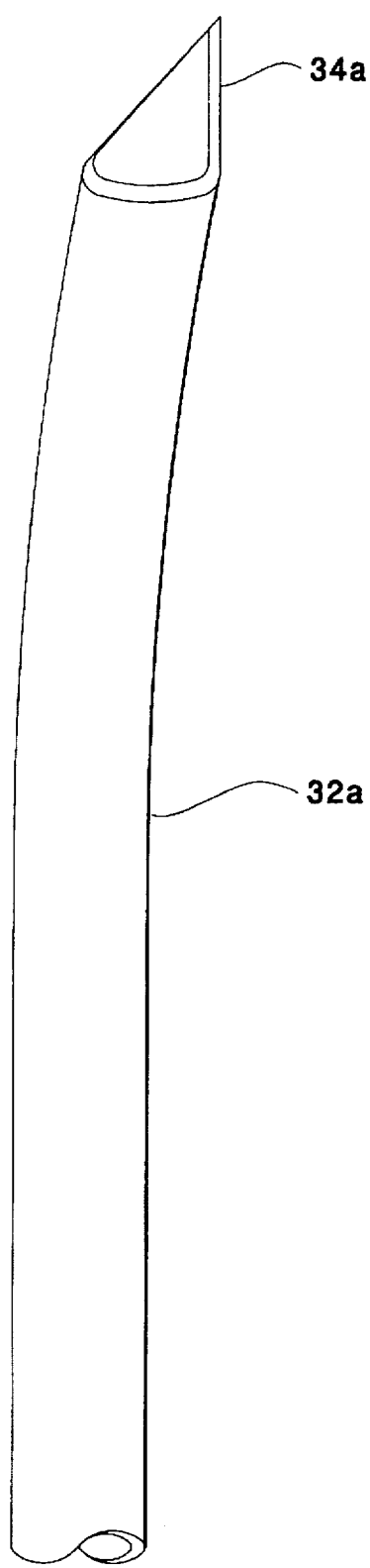
FIG. 4 is alternative embodiment of the portion of the intravenous catheter shown in FIG. 3.

FIG. 3 shows in detail shaft 32 of catheter 30, in which point 34 is a double bilateral v-shaped tip. In the alternative embodiment shown in FIG. 4, shaft 32a and point 34a are slightly bent to prevent coring.

The use of a shape memory polymer for the tip is especially advantageous in situations where the patient bends the arm during insertion. With the shape memory polymer, the tip of the catheter bends with the arm, but returns to its original straight shape, preventing kinking of the tip and possible backing up of fluid causing infiltration of the vein.

The principle on which the invention is based, use of a polymer which can pierce the skin but which softens when exposed to body temperature and/or fluids, can be applied to a wide variety of medical devices in which a metal needle, guidewire or lancet is normally used to enter a body cavity. Among these devices are SWAN GANZ catheters, central line catheters, peripheral catheters, dialysis catheters, thermodilution catheters, peripherally inserted central line catheters, midline catheters, hemodilution catheters, blood sampling catheters, endotracheal tubes, bronchial catheters, chest tubes, nasogastric tubes, gastric tubes, body drains, suprapubic tubes, intramuscular devices, intradermal devices, intrathecal devices, subcutaneous devices, body stents, shunts, suction devices, tracheotomy devices and biopsy devices. The invention can also be used in connection with medical procedures including angioplasty, diagnostic procedures, arteriograms, arthroscopy, lumbar puncture, laparoscopy and fluoroscopy. These examples do not limit the scope of the invention which can be used in connection with other devices and procedures.

What is claimed is:

1. A medical device for introducing fluid treating material to or removing a fluid material from a body cavity of a human or animal, comprising:

a hollow, needle-like structure having a proximal end and a distal end, said proximal end having a tip beveled to a shape point and said needle-like structure being formed from a polymer which is sufficiently rigid at ambient temperature to permit puncture of skin by said point, and which becomes soft after a predetermined period of time exposed to body temperature and body fluids, thus preventing bodily trauma; and a hub attached to the distal end of said hollow needle-like structure and having a diameter greater than that of said hollow needle-like structure, said hub including connector means for attachment of a handle or a device for introducing fluid treating material to or removing fluid from the body cavity.

2. A medical device according to claim 1, wherein said beveled tip is non-coring.

3. A medical device according to claim 2, wherein said polymer has a glass transition temperature of about 25°–55° C.

4. A medical device according to claim 3, wherein said polymer has a glass transition temperature of about 40° C.

5. A medical device according to claim 1, wherein said polymer is a polyurethane, hydrogel or a polyethylene oxide.

6. A medical device according to claim 5, wherein said polymer is a shape memory polyurethane.

7. A medical device according to claim 1, wherein said polymer has a glass transition temperature of about 25°–55° C.

8. A medical device according to claim 7, wherein said glass transition temperature is about 40° C.

9. A medical device according to claim 1, wherein said polymer is a biocompatible shape memory polymer.

10. A medical device according to claim 1, wherein the period of time is about 2–9 minutes.

11. A medical device according to claim 1, wherein the period of time is about 10–90 minutes.

12. A medical device according to claim 1, additionally comprising a valve interposed in said hub between said needle-like structure and said connector means, said valve including means permitting flow of fluid only when a device for introducing or a device for removing is attached to said connector means.

13. A medical device according to claim 1, wherein said hub formed of a transparent or translucent polymer.

14. A medical device according to claim 1, wherein said connector means is a LUER connector.

15. A medical device according to claim 1, wherein said beveled tip is a double bilateral v-shaped coring or non-coring tip.

16. A medical device according to claim 1, wherein said polymer possesses the property of remaining soft after removal from body temperature and body fluids to prevent reuse.

17. A medical device for introducing fluid treating material to or removing a fluid material from a body cavity of a human or animal, comprising:

a hollow, needle-like structure having a proximal end and a distal end, said proximal end having a coring or non-coring tip beveled to a shape point and said structure being formed form a polymer which is sufficiently rigid at ambient temperature to permit puncture of skin by said point, and which becomes soft after a predetermined period of time exposed to body temperature and body fluids, thus preventing bodily trauma;

a hub attached to the distal end of said hollow needle-like structure and having a diameter greater than that of said hollow needle-like structure, said hub having a proximal end attached to the distal end of said hollow needle-like structure, and a distal end including connector means for attachment of a handle or a device for introducing fluid treating material to or removing fluid from the body cavity; and a valve interposed in said hub between said proximal end and said distal end, said valve including means permitting flow of fluid only when a device for introducing or a device for removing is attached to said means for attaching.

18. A medical device according to claim 17 wherein said valve comprises:

a stationary disk of self-sealing material spaced from the proximal end of said hub and forming a proximal chamber adjacent the proximal end of said hub and a distal chamber adjacent the distal end of said hub, said disk blocking fluid flow between said chambers;

a second disk spaced from the distal end of said hub; and a spring loaded, movable hollow puncture means having a first end projecting through said second disk and a second, piercing end constructed and arranged to rest on the distal side of said disk of self-sealing material with said spring in a rest position, and constructed and arranged to move in a proximal direction and pierce said disk of self-sealing material and allow fluid flow therethrough when said spring is compressed upon attachment of the device for introducing or removing fluid.

19. A medical device according to claim 17, wherein the second, piercing end of said puncture means comprises a non-coring tip.

20. A medical device according to claim 17, additionally comprising a removable handle having a proximal end and a distal end, said proximal end including connector means for attachment to the connector means of said hub.

21. A medical device according to claim 20, wherein the distal end of said handle comprises a connector means, and the handle further comprises a removable cap having a connector means constructed and arranged for attachment to the connector means of the distal end of said handle and to the connector means of the distal end of said hub.

22. A medical device according to claim 17, wherein said polymer is a polyurethane or a polyethylene oxide.

23. A medical device according to claim 22, wherein said polymer is a shape memory polyurethane.

24. A medical device according to claim 17, wherein said polymer is a biocompatible shape memory polymer.

25. A medical device according to claim 17, wherein the period of time is about 2–9 minutes.

26. A medical device according to claim 17, wherein the period of time is about 10–90 minutes.

27. A medical device according to claim 17, wherein said polymer possesses the property of remaining soft after insertion to prevent reuse.

* * * * *

UNITED STATES PATENT AND TRADEMARK OFFICE
CERTIFICATE OF CORRECTION

PATENT NO. : 5,634,913
DATED : June 3, 1997
INVENTOR(S) : Florence Stinger

It is certified that error appears in the above-indentified patent and that said Letters Patent is hereby corrected as shown below:

In the Claims:

Claim 17, Col. 7, line 54, change "shape" to --sharp--

Signed and Sealed this

Fifth Day of August, 1997

Attest:

BRUCE LEHMAN

*Attesting Officer*                *Commissioner of Patents and Trademarks*

UNITED STATES PATENT AND TRADEMARK OFFICE
CERTIFICATE OF CORRECTION

PATENT NO. : 5,634,913
DATED : June 3, 1997
INVENTOR(S) : Florence Stinger

It is certified that error appears in the above-identified patent and that said Letters Patent is hereby corrected as shown below:

Column 4, lines 32-33, change "Port-a-Catch Catheter" to --PORT-A-CATH catheter--

Signed and Sealed this

Second Day of June, 1998

Attest:

BRUCE LEHMAN

Attesting Officer  Commissioner of Patents and Trademarks